(12) United States Patent
Sauerland et al.

(10) Patent No.: US 10,098,838 B2
(45) Date of Patent: Oct. 16, 2018

(54) WATER-SOLUBLE GRANULAR MATERIAL FOR PRODUCING A DRINKING SOLTUION

(71) Applicant: Sanofi-Aventis Deutschland GmbH, Frankfurt am Main (DE)

(72) Inventors: Sandra Sauerland, Ummendorf (DE); Sonja Heigenhauser, Ulm (DE); Uwe Scheuring, Ochsenhausen-Hattenburg (DE); Oliver Timm, Ummendorf (DE)

(73) Assignee: SANOFI-AVENTIS DEUTSCHLAND GMBH, Paris (FR)

( * ) Notice: Subject to any disclaimer, the term of this patent is extended or adjusted under 35 U.S.C. 154(b) by 0 days.

(21) Appl. No.: 15/503,184

(22) PCT Filed: Jul. 21, 2015

(86) PCT No.: PCT/EP2015/066659
§ 371 (c)(1),
(2) Date: Feb. 10, 2017

(87) PCT Pub. No.: WO2016/023714
PCT Pub. Date: Feb. 18, 2016

(65) Prior Publication Data
US 2017/0231907 A1    Aug. 17, 2017

(30) Foreign Application Priority Data

Aug. 12, 2014 (DE) .................. 20 2014 006 415 U

(51) Int. Cl.
| | |
|---|---|
| *A61K 36/87* | (2006.01) |
| *A61K 9/00* | (2006.01) |
| *A61K 9/16* | (2006.01) |
| *B65D 75/54* | (2006.01) |
| *B65D 85/60* | (2006.01) |

(52) U.S. Cl.
CPC .......... *A61K 9/0095* (2013.01); *A61K 9/1611* (2013.01); *A61K 9/1617* (2013.01); *A61K 9/1623* (2013.01); *A61K 9/1652* (2013.01); *A61K 36/87* (2013.01); *B65D 75/54* (2013.01); *B65D 85/60* (2013.01); *A61K 2236/15* (2013.01); *A61K 2236/30* (2013.01)

(58) Field of Classification Search
CPC .............................. A61K 9/0095; A61K 36/87
See application file for complete search history.

(56) References Cited

U.S. PATENT DOCUMENTS

| | | | | |
|---|---|---|---|---|
| 2013/0210754 A1* | 8/2013 | Scheuring | .............. | A61K 36/87 514/27 |
| 2016/0184223 A1* | 6/2016 | Cleverly | .............. | A61K 9/0056 514/28 |

FOREIGN PATENT DOCUMENTS

| | | | | |
|---|---|---|---|---|
| EP | 1550450 | A1 | * | 7/2005 |
| EP | 2322158 | | * | 5/2011 |
| EP | 2322158 | A2 | | 5/2011 |
| JP | 2005/052085 | | * | 3/2005 |
| JP | 4778004 | | * | 9/2011 |

OTHER PUBLICATIONS

International Search Report and the Written Opinion for PCT/EP2015/066659 dated Sep. 17, 2015, 12 pages.
XP002744600, Database WPI, Thomson Scientific, London, GB; Mar. 3, 2005, 2 pages.

* cited by examiner

*Primary Examiner* — Ralph J Gitomer
(74) *Attorney, Agent, or Firm* — Edell, Shapiro & Finnan, LLC

(57) ABSTRACT

The invention relates to water-soluble granules for preparing a drinkable solution, in particular for preventing or treating symptoms associated with mild to moderate chronic venous insufficiency of the lower extremities, containing at least 20 percent by weight of a concentrated extract of red wine leaves, and to a ready-to-use packaging unit comprising one or more portion sachets which contain the granules according to the invention.

9 Claims, No Drawings

WATER-SOLUBLE GRANULAR MATERIAL FOR PRODUCING A DRINKING SOLTUION

PRIORITY APPLICATION

The complete disclosure of the underlying utility model application DE 20 2014 006 415.6 of Dec. 8, 2014, priority of which is claimed herein, is incorporated herein by reference.

BACKGROUND OF THE INVENTION

1. Technical Field

The invention relates to water-soluble granules for preparing a drinkable solution, in particular for preventing or treating symptoms associated with mild to moderate chronic venous insufficiency of the lower extremities, containing at least 20 percent by weight of a concentrated extract of red vine leaves.

2. Prior Art

German Patent DE 600 27 481 proposes a composition, which is in a form suitable for oral administration, for treating chronic venous insufficiency using an extract of red vine leaves.

German Patent DE 603 32 767 describes a film-coated tablet comprising an extract of red vine leaves.

The EMA "Assessment Report on *Vitis vinifera* L., folium" (EMA/HMPC/16633/2009) of 15 Jul. 2010 summarises the preclinical and clinical data relating to the well-established and traditional use of red vine leaves.

The dietary supplement "Programme Jambes Légères" from Yves Rocher consists of drinkable granules which contain, in addition to 10 percent by weight of an extract of hibiscus flowers and natural blueberry flavouring, approximately 5 percent by weight of an extract of red vine leaves.

However, the content of active substance in this product is too low to achieve a significant effect in preventing or treating symptoms associated with mild to moderate chronic venous insufficiency of the lower extremities.

The present invention was based on the object of providing delicious water-soluble granules containing an extract of red vine leaves for preparing a drinkable solution which is suitable for preventing or treating symptoms associated with mild to moderate chronic venous insufficiency of the lower extremities.

A further requirement is a long storage stability of the granules without a substantial reduction in the content of the flavonoids of the extract.

Said granules should furthermore be accepted by users with respect to taste, where appropriate also without the addition of artificial or natural flavouring agents, in order to achieve high compliance.

It has now been found, surprisingly, that water-soluble granules consisting of at least 20 percent by weight of a concentrated extract of red vine leaves, a water-soluble carrier material, an acidifying agent, a flow regulating agent and a sweetening agent are outstandingly suitable for preparing a drinkable solution for preventing or treating symptoms associated with mild to moderate chronic venous insufficiency of the lower extremities.

The main feature of the granules in this case is the rapid and complete dissolution in hot or cold liquids, such as water, tea or fruit juices. This is achieved by coarse granules of a porous structure.

It has furthermore been found, surprisingly, that the granules according to the invention have a high anti-oxidising action.

BRIEF SUMMARY OF THE INVENTION

The invention thus provides water-soluble granules for preparing a drinkable solution consisting of a concentrated extract of red vine leaves, a water-soluble carrier material, an acidifying agent, a flow regulating agent, a sweetening agent and optionally a flavouring agent, the granules containing at least 20 percent by weight of the extract of red vine leaves.

A further aspect of the invention is a method for preventing or treating symptoms associated with mild to moderate chronic venous insufficiency of the lower extremities or for improving microvascular blood flow, this method comprising administering to a person an aqueous drinkable solution obtainable by mixing granules consisting
of a concentrated extract of red vine leaves, a water-soluble carrier material, an acidifying agent, a flow regulating agent, a sweetening agent and optionally a flavouring agent,
the granules containing at least 20 percent by weight of the extract of red vine leaves,
with water or an aqueous drink.

The invention further provides a ready-to-use packaging unit substantially consisting of
(A) one or more sealed portion sachets containing 500 to 1,000, preferably 700 to 900, in particular approximately 800 mg, of granules according to the invention; and
(B) a package insert which explains the opening of the portion sachets (A) and the amount of water or drink in which the granules are to be dissolved, as well as, where appropriate, the use for preventing or treating symptoms associated with mild to moderate chronic venous insufficiency of the lower extremities or for improving microvascular blood flow.

DETAILED DESCRIPTION OF THE INVENTION

The term "concentrated extract of red vine leaves" as used above and below relates to an aqueous extract of red leaves of the vine such as is described, for example, in the above-mentioned EMA Assessment Report EMA/HMPC/16633/2009.

This extract is obtainable, for example, by
(a) collecting red vine leaves at a time at which the flavonoid content reaches an optimum;
(b) drying and crushing the leaves;
(c) cutting the leaves into pieces;
(d) extracting the leaves using water at temperatures of from 60 to 80° C. for 6 to 10 hours by complete percolation;
(e) concentrating the extract obtained.

In particular, this is the dry extract of *Vitis vinifera* L., folium (4-6:1; water) described in the Assessment Report.

The term "granules" as used above and below relates to a granular to pulverulent, readily pourable, solid composition, preferably a coarse composition having a porous structure. As a rule, said granules are obtained by granulation, in particular by wet granulation, the individual constituents being made into a suspension and this wet material then being crushed and dried, or by dry granulation or roller compaction, in which a powder of the premixed constituents is driven through a gap between two rollers. The formed flakes are then crushed again on a sieve. Fluid bed granulation in which water is added to a powder of the premixed constituents on an air bed is also used.

Finally, the granules according to the invention can also be produced by subjecting a wet mixture of all or some of the constituents, in particular a mixture of the extract and the water-soluble carrier material, to a spray drying process.

If only some of the constituents are granulated, the other components can be added later in dry form to the original granules.

Preferred embodiments of the granules according to the invention are those in which:

(i) they contain 20 to 80, preferably 40 to 75, in particular 45 to 60, percent by weight of a dried, aqueous extract of red vine leaves, in particular the dry extract of *Vitis vinifera* L., folium (4-6:1; water) according to EMA/HMPC/16633/2009; particularly preferably, the granules contain, based on an individual portion, for example a powder sachet, 300 to 500 mg, preferably 320 to 400 mg, in particular 355 to 380 mg, most preferably approximately 360 mg, of the dry extract of *Vitis vinifera* L., folium (4-6:1; water) according to EMA/HMPC/16633/2009;

(ii) the water-soluble carrier material is a carbohydrate mixture, in particular maltodextrin, the weight ratio between the dried, aqueous extract of red vine leaves and the water-soluble carrier material preferably being 0.5:1.0 to 2.0:1.0, in particular 0.8:1.0 to 1.2:1.0;

(iii) the acidifying agent is an organic acid selected from the group consisting of malic acid, citric acid, ascorbic acid, lactic acid and tartaric acid, in particular tartaric acid. Preferably, the pH of the resulting drinkable solution when dissolved in neutral water is below pH 6, in particular pH 3.0 to pH 5.5;

(iv) the flow regulating agent is colloidal silicon dioxide;

(v) the sweetening agent is a sweetener selected from the group consisting of acesulfame, aspartame, cyclamate, neohesperidin, saccharin, sucralose, stevioside and thaumatin, in particular sucralose.

In addition to the constituents mentioned the granules can also contain one or more artificial or natural flavouring agents. Herb, tea and fruit flavourings, in particular in solid form, are preferred. The following flavourings are preferred: peppermint, tea, grape, blackberry, raspberry, blueberry, wild strawberry, cherry, blackcurrant, plum, cranberry, grenadine and lime, in particular lime. Granules according to the invention are very particularly preferably free from additional flavouring agents.

Preferably, the granules according to the invention substantially consist of 20 to 80 wt. % of the dried, aqueous extract of red vine leaves, 20 to 80 wt. % of a water-soluble carrier material, 8 to 20 wt. % of an acidifying agent, 0.5 to 1.5 wt. % of a flow regulating agent, 0.2 to 0.8 wt. % of a sweetening agent and optionally up to 2.0 wt. % of a flavouring agent, these constituents together amounting to 100 percent by weight;

(vi) they substantially consist of the following constituents:

| Content in wt. % | Constituent |
| --- | --- |
| 20-80 | concentrated extract of red vine leaves |
| 20-80 | maltodextrin |
| 8-20 | tartaric acid |
| 0.5-1.5 | anhydrous colloidal silicon dioxide |
| 0.2-0.8 | sucralose |
| 0-2.0 | lime flavouring | these constituents together amounting to 100 percent by weight;

(vii) they are used for preparing a drinkable solution for preventing or treating symptoms associated with mild to moderate chronic venous insufficiency of the lower extremities or for improving microvascular blood flow;

(viii) they are used for preparing a dietary supplement in the form of a drinkable solution for improving metabolism by reducing the amount of free radicals.

Preferably, the drinkable granules according to the invention are filled into portion-sized powder sachets. As a rule, these sachets contain 500 to 1,000, preferably 700 to 900, in particular approximately 800, mg of granules according to the invention. They are manufactured from non-coated or coated aluminium laminate, in particular aluminium laminate coated with Surlyn® from DuPont, and have a length of from 5.0 to 10.0 cm, preferably 6.0 to 8.0, in particular approximately 7.5 cm, and a width of from 1.0 to 3.0 cm, preferably 1.5 to 2.5, in particular approximately 2.0 cm. They furthermore have a notch at one end which makes it easier to open the sachets.

Example 1

Granules are produced and filled into powder sachets, each powder sachet containing granules consisting of the following constituents:

| Constituent | Content in mg |
| --- | --- |
| Concentrated extract of red vine (leaves 4-6:1; water) | 360 |
| Maltodextrin | 360 |
| Tartaric acid | 75 |
| Anhydrous colloidal silicon dioxide | 8 |
| Sucralose | 5 |

For this, the appropriate amount of maltodextrin is added in small portions to the thick extract of red vine leaves and these components are mixed with one another. The wet mixture is sprayed in a spray dryer to form dry granules. The granules are then mixed with the remaining constituents and filled into sachets.

The drinkable granules contained in a powder sachet dissolve within from 30 to 40 seconds in 100-200 ml of hot or cold liquid, such as water, tea or fruit juice. In a consumer test conducted in Italy the obtained drinkable solution was found to be pleasant in taste and delicious by all the test subjects and is outstandingly suitable for alleviating the symptoms associated with mild to moderate chronic venous insufficiency of the lower extremities.

Example 2

Granules are produced and filled into powder sachets, each powder sachet containing granules consisting of the following constituents:

| Constituent | Content in mg |
| --- | --- |
| Concentrated extract of red vine leaves (4-6:1; water) | 360 |
| Maltodextrin | 360 |
| Tartaric acid | 75 |
| Anhydrous colloidal silicon dioxide | 8 |
| Sucralose | 5 |
| Lime flavouring | 8 |

For this, the appropriate amount of maltodextrin is added in small portions to the thick extract of red vine leaves and these components are mixed with one another. The wet mixture is sprayed in a spray dryer to form dry granules. The granules are then mixed with the remaining constituents and filled into sachets.

The drinkable granules contained in a powder sachet dissolve rapidly in 100-200 ml of hot or cold liquid, such as water, tea or fruit juice. In a consumer test conducted in Italy the obtained drinkable solution was found to be very pleasant in taste and delicious by all the test subjects and is outstandingly suitable for alleviating the symptoms associated with mild to moderate chronic venous insufficiency of the lower extremities.

Example 3

Consumer Test 202 test subjects received the drinkable granules according to the invention (102 received granules according to Example 1, 100 received granules according to Example 2) and after tasting were asked how much they liked the taste of the resulting drink. The following results were achieved in this test:

| Taste | Example 1 | Example 2 |
| --- | --- | --- |
| Very good | 13 | 14 |
| Good | 70 | 71 |
| Neither good nor poor | 14 | 12 |
| Poor | 4 | 2 |
| Very poor | 1 | 1 |

Example 4

Investigation of the Antioxidative Action

The ORAC (=oxygen radical absorbance capacity) test is a standardised method for determining the capacity of natural substances for trapping oxygen radicals and is stated in Trolox equivalents ($\mu$mol TE/100 g). The measurement principle is a measurement of the fluorescence of the dye fluorescein up to exhaustion thereof by a synthetic generator of radicals. An added antioxidant delays the oxidation of the fluorescein, and the higher the capacity, the greater the area measured under the time curve (AUC). A description can be found, for example, on Wikipedia: http://www.en.wikipedia.org/wiki/Oxygen radical absorbance capacity.

The Institut Prof. Kurz GmbH in 50933 Köln (www.institut-kurz.de) accredited for this was commissioned to perform the ORAC tests and carried out the measurements by means of fluorimetric IK2002-hydrophilic microtiter plate tests.

In a test series in March 2015, the granules according to the invention comprising 360 mg of active principle were tested against other commercially available finished products. The results are reproduced in the following table:

| Product | ORAC value [$\mu$mol TE/100 g] |
| --- | --- |
| Granules according to the invention (batch 1) | 170500 |
| Granules according to the invention (batch 2) | 177900 |
| Pycnogenol ® (pine bark extract) 50 mg GPH capsules, Hecht-Pharma GmbH, PZN 09188092 | 161700 |
| Vitamin C 200 mg tablets, medphano Arzneimittel GmbH, PZN 04588935 | 108000 |

The ORAC value of the two samples according to the invention is of the same order of magnitude, and is even also a little higher than that of Pycnogenol®, which is one of the most investigated antioxidants. Vitamin C, which is likewise used as an antioxidant, has an ORAC value which is approximately 40% lower.

The invention claimed is:

1. Water-soluble granules for preparing a drinkable solution, the water-soluble granules consisting of a concentrated extract of red vine leaves, a water-soluble carrier material, an acidifying agent, 0.5% to 1.5% by weight of a flow regulating agent comprising colloidal silica, a sweetening agent and optionally a flavouring agent, wherein the granules contain 45% to 60% by weight of the extract of red vine leaves, and wherein the granules, when dissolved in neutral water, form a drinkable solution having a pH from 3.0 to 5.5.

2. Granules according to claim 1, wherein the extract of red vine leaves is obtainable by a process which comprises the following steps:
   (a) collecting red vine leaves at a time at which the flavonoid content reaches an optimum;
   (b) drying and crushing the leaves;
   (c) cutting the leaves into pieces;
   (d) extracting the leaves using water at temperatures of from 60 to 80° C. for 6 to 10 hours by percolation;
   (e) concentrating the extract obtained.

3. Granules according to claim 1, wherein the water-soluble carrier material comprises maltodextrin.

4. Granules according to claim 1, wherein the acidifying agent is an organic acid selected from the group consisting of malic acid, citric acid, ascorbic acid, lactic acid and tartaric acid.

5. Granules according to claim 1, wherein the sweetening agent is a sweetener selected from the group consisting of acesulfame, aspartame, cyclamate, neohesperidin, saccharin, sucralose, stevioside and thaumatin.

6. Granules according to claim 1, wherein the granules consist essentially of the following constituents:

| Content in wt. % | Constituent |
| --- | --- |
| 45-60 | concentrated extract of red vine leaves |
| 20-80 | maltodextrin |
| 8-20 | tartaric acid |
| 0.5-1.5 | anhydrous colloidal silicon dioxide |
| 0.2-0.8 | sucralose |
| 0-2.0 | lime flavouring | wherein the constituents together amount to 100 percent by weight.

7. Granules according to claim 1 for preparing a drinkable solution for preventing or treating symptoms associated with mild to moderate chronic venous insufficiency of the lower extremities or for improving microvascular blood flow.

8. Granules according to claim 1 for preparing a dietary supplement in the form of a drinkable solution for improving metabolism by reducing the amount of free radicals.

9. A ready-to-use packaging unit consisting substantially of
  (A) one or more sealed portion sachets containing 500 to 1,000 mg of granules according to claim 1; and
  (B) a packaging insert which explains the opening of the portion sachets (A) and the amount of water or drink in which the granules are to be dissolved, as well as, where appropriate, the use for preventing or treating symptoms associated with mild to moderate chronic venous insufficiency of the lower extremities or for improving microvascular blood flow.

\* \* \* \* \*